US010585552B2

(12) United States Patent
Merdan et al.

(10) Patent No.: US 10,585,552 B2
(45) Date of Patent: Mar. 10, 2020

(54) DISTRIBUTED INTERACTIVE MEDICAL VISUALIZATION SYSTEM WITH USER INTERFACE FEATURES

(71) Applicant: Boston Scientific Scimed, Inc., Maple Grove, MN (US)

(72) Inventors: Kenneth Matthew Merdan, Loretto, MN (US); David M. Flynn, Lino Lakes, MN (US); Gregory Ernest Ostenson, St. Paul, MN (US); Benjamin Bidne, Hanover, MN (US); Robbie Halvorson, Plymouth, MN (US); Eric A. Ware, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 15/671,873

(22) Filed: Aug. 8, 2017

(65) Prior Publication Data
US 2018/0046355 A1    Feb. 15, 2018

Related U.S. Application Data

(60) Provisional application No. 62/374,343, filed on Aug. 12, 2016.

(51) Int. Cl.
G06F 3/0481    (2013.01)
G16H 80/00    (2018.01)
(Continued)

(52) U.S. Cl.
CPC ........ G06F 3/04815 (2013.01); A61B 5/7435 (2013.01); G06F 3/03542 (2013.01);
(Continued)

(58) Field of Classification Search
CPC ................. G06T 19/20; G06T 2210/41; G06T 2219/024; G06T 2219/028; G06T 19/006;
(Continued)

(56) References Cited

U.S. PATENT DOCUMENTS 5,494,042 A    2/1996 Panescu et al.
6,608,628 B1    8/2003 Ross et al.
(Continued)

FOREIGN PATENT DOCUMENTS

CN    106456250    2/2017
DE    102007028065    1/2009
(Continued)

OTHER PUBLICATIONS

"3D Medical Animation Demo—Cardiac Catheterization," Published on Aug. 3, 2012. <https://www.youtube.com/watch?v=hXdNY97Xkmw>.
(Continued)

Primary Examiner — Yingchun He
(74) Attorney, Agent, or Firm — Pauly, DeVries Smith & Deffner LLC

(57) ABSTRACT

Embodiments herein relate to distributed interactive medical visualization systems including user interface features and related methods. In an embodiment, a distributed interactive medical visualization system is included having a first video processing circuit, a first central processing circuit in communication with the first video processing circuit, a first communications circuit in communication with the first central processing circuit, and a first user interface generated by the first video processing circuit. The first user interface can include a three-dimensional model of at least a portion of a subject's anatomy from a first perspective, the first perspective configured to be controlled by a first user. The first user interface can further include one or more user
(Continued)

representations representing one or more other users, the user representations superimposed within the three-dimensional model, wherein each of the one or more user representations are visually distinct from one another. Other embodiments are also included herein.

11 Claims, 9 Drawing Sheets

(51) Int. Cl.
| | | |
|---|---|---|
| *G16H 50/50* | (2018.01) | |
| *G06T 19/00* | (2011.01) | |
| *G06T 15/20* | (2011.01) | |
| *G06F 3/14* | (2006.01) | |
| *G06F 3/0484* | (2013.01) | |
| *G06F 3/0354* | (2013.01) | |
| *A61B 5/00* | (2006.01) | |

(52) U.S. Cl.
CPC ........ *G06F 3/04845* (2013.01); *G06F 3/1454* (2013.01); *G06T 15/20* (2013.01); *G06T 19/00* (2013.01); *G16H 50/50* (2018.01); *G16H 80/00* (2018.01); *G06T 2210/41* (2013.01); *G06T 2219/004* (2013.01); *G06T 2219/024* (2013.01)

(58) Field of Classification Search
CPC .. G06F 19/321; G06F 19/3481; G06F 17/241; H04L 12/1822
See application file for complete search history.

(56) References Cited

U.S. PATENT DOCUMENTS

| | | |
|---|---|---|
| 7,291,166 B2 | 11/2007 | Cheng et al. |
| 7,840,393 B1 | 11/2010 | Whirley et al. |
| 8,363,096 B1 | 1/2013 | Aguirre-Valencia |
| 8,958,615 B2 | 2/2015 | Blum et al. |
| 9,333,361 B2 | 5/2016 | Li et al. |
| 9,364,665 B2 | 6/2016 | Bokil et al. |
| 9,411,935 B2 | 8/2016 | Moffitt et al. |
| 2003/0212321 A1 | 11/2003 | Baxter, III |
| 2003/0216710 A1 | 11/2003 | Hurt |
| 2004/0049115 A1 | 3/2004 | Murphy et al. |
| 2004/0097805 A1 | 5/2004 | Verard et al. |
| 2004/0257361 A1 | 12/2004 | David Tabakman et al. |
| 2006/0100502 A1 | 5/2006 | Chen et al. |
| 2006/0290695 A1 | 12/2006 | Salomie |
| 2007/0043466 A1 | 2/2007 | Vesely et al. |
| 2007/0092864 A1 | 4/2007 | Reinhardt et al. |
| 2007/0127791 A1 | 6/2007 | Ernvik et al. |
| 2007/0185485 A1 | 8/2007 | Hauck et al. |
| 2007/0248261 A1 | 10/2007 | Zhou et al. |
| 2008/0137926 A1 | 6/2008 | Skinner et al. |
| 2009/0062642 A1 | 3/2009 | Hauck |
| 2009/0287186 A1 | 11/2009 | Adams et al. |
| 2010/0067768 A1 | 3/2010 | Ionasec et al. |
| 2010/0094370 A1 | 4/2010 | Levin et al. |
| 2010/0106475 A1 | 4/2010 | Smith et al. |
| 2010/0290679 A1 | 11/2010 | Gasser et al. |
| 2010/0318326 A1 | 12/2010 | Yamamoto |
| 2011/0170752 A1 | 7/2011 | Martin et al. |
| 2012/0296392 A1 | 11/2012 | Lee et al. |
| 2013/0073619 A1 | 3/2013 | Tumuluri et al. |
| 2013/0128011 A1 | 5/2013 | Tu et al. |
| 2013/0172732 A1 | 7/2013 | Kiraly et al. |
| 2013/0234934 A1 | 9/2013 | Champion et al. |
| 2013/0296845 A1 | 11/2013 | Bar-Tal et al. |
| 2014/0225887 A1 | 8/2014 | Aguirre-Valencia |
| 2015/0049081 A1 | 2/2015 | Coffey et al. |
| 2015/0049082 A1 | 2/2015 | Coffey et al. |
| 2015/0049083 A1 | 2/2015 | Bidne et al. |
| 2015/0134031 A1 | 5/2015 | Moffitt et al. |
| 2015/0347682 A1* | 12/2015 | Chen ................ G16H 50/30 705/2 |
| 2016/0081658 A1 | 3/2016 | Perrey et al. |
| 2016/0151634 A1 | 6/2016 | Carcieri et al. |
| 2016/0225152 A1 | 8/2016 | Blum et al. |
| 2016/0255086 A1 | 9/2016 | Vajravelu et al. |
| 2016/0353055 A1* | 12/2016 | Popescu ................ G06T 19/006 |
| 2017/0234934 A1 | 8/2017 | Zhong et al. |
| 2017/0367771 A1 | 12/2017 | Tako et al. |
| 2018/0046354 A1 | 2/2018 | Merdan et al. |

FOREIGN PATENT DOCUMENTS

| | | |
|---|---|---|
| EP | 2605824 | 6/2013 |
| EP | 2630987 | 8/2013 |
| EP | 2691898 | 2/2014 |
| EP | 2691899 | 2/2014 |
| EP | 2691900 | 2/2014 |
| EP | 2714187 | 4/2014 |
| EP | 2741817 | 6/2014 |
| EP | 2742482 | 6/2014 |
| EP | 2765776 | 8/2014 |
| EP | 2890451 | 7/2015 |
| EP | 2891091 | 7/2015 |
| EP | 3035884 | 6/2016 |
| EP | 2709721 | 9/2016 |
| JP | 2016527994 | 9/2016 |
| WO | 2012024441 | 2/2012 |
| WO | 2012135190 | 10/2012 |
| WO | 2012135191 | 10/2012 |
| WO | 2012135198 | 10/2012 |
| WO | 2012158882 | 11/2012 |
| WO | 2012166656 | 12/2012 |
| WO | 2013023073 | 2/2013 |
| WO | 2013023076 | 2/2013 |
| WO | 2014036079 | 3/2014 |
| WO | 2014036081 | 3/2014 |
| WO | 2015023787 | 2/2015 |
| WO | 2015149042 | 10/2015 |
| WO | 2018031558 | 2/2018 |
| WO | 2018031561 | 2/2018 |

OTHER PUBLICATIONS

Brock, Michael "Virtual Reality Among Hottest Tech Tectors to Watch at CES 2016," VR Journal, Jan. 2016 URL <http://vrjournal.com/virtual-reality-among-hottest-tech-sectors-to-watch-at-ces-2016/> (5 pages).

Brugger, Tim "Who's Ready for Virtual Reality? Turns Out, Most Everyone," Fool.com Technology and Telecom Dec. 14, 2015 URL <http://www.fool.com/investing/general/2015/12/14/whos-ready-for-virtual-reality-turns-out-most-ever.aspx?source+eogyholnk0000001&utm_source=yahoo&utm_medium=feed&utm_campaign=article> (4 pages).

Carvalho, Diego D. et al., "Estimating 3D lumen centerlines of carotid arteries in free-hand acquisition ultrasound," International Journal of Computer Assisted Radiology and Surgery, vol. 7, No. 2, Jun. 2011 (9 pages).

Coffey, Dane et al., "Interactive Slice WIM: Navigating and Interrogating Volume Data Sets Using a Multisurface, Multitouch VR Interface," Visualization and Computer Graphics, IEEE Transactions on, vol. 18, pp. 1614-1626, 2012 (13 pages).

Coffey, Dane et al., "Low Cost VR Meets Low Cost Multi-touch," Proceedings of the international Symposium on Visual Computing, Springer Lecture Notes in Computer Science, vol. 6454, pp. 351-360, Nov. 2010 (10 pages).

Coffey, Dane et al., "Slice WIM: A Multi-Surface, Multi-Touch Interface for Overview + Detail Exploration of Volume Datasets in Virtual Reality," presented at the Symposium on Interactive 3D Graphics and Games, San Francisco, California, Feb. 2011 (8 pages).

Cohen, Elizabeth "Google Cardboard Saves Baby's Life," CNN video, Jan. 7, 2016 URL <http://www.cnn.com/2016/01/07/health/google-cardboard-baby-saved/index.html>.

(56) References Cited

OTHER PUBLICATIONS

"EchoPixel: Hospital Holograms Bring Doctors Into New Era," Bloomberg Mar. 16, 2015 URL <http://www.bloomberg.com/news/videos/2015-03-16/echopixel-hospital-holograms-bring-doctors-into-new-era> (1 page).

Erdman, Arthur G. "Grand Challenge: applying Regulatory Science and Big Data to Improve Medical Device Innovation," IEEE Transactions on Biomedical Engineering, 60(3), pp. 700-706, Mar. 2013 (7 pages).

File History for U.S. Appl. No. 14/459,129 downloaded Sep. 14, 2017 (1244 pages).

File History for U.S. Appl. No. 14/459,163 downloaded Sep. 14, 2017 (1525 pages).

File History for U.S. Appl. No. 14/459,202 downloaded Sep. 14, 2017 (1513 pages).

File History for European Patent Application No. 14758043.5 downloaded Sep. 14, 2017 (455 pages).

"First-in-man use of virtual reality imaging in cardiac cath lab to treat blocked coronary artery," Elsevier Health Sciences, Nov. 20, 2015 URL <Http://www.eurekalert.org/pub_releases/2015-11/ehs-fuo111815.php#.Vo1R81ipUAk.mailto> (3 pages).

Fornell, Dave "Editor's Choice of Most Innovative New Technology at RSNA 2015," Diagnostic and Interventional Cardiology Dicardiology.com 2015 URL <http://www.dicardiology.com/videos/editors-choice-most-innovative-new-technology-rsna-2015> (1 page).

Gruber, Ben "Body Parts Floating in 3D Space to Give Medicine Virtual Shape," Thomson Reuters Science News Sep. 21, 2015 URL <http://www.reuters.com/article/us-usa-virtual-medicine-tracked-idUSKCN0RL1W320150921> (3 pages).

"Hp Zvr 23.6-inch Virtual Reality Display (K5H59A8)," HP Product Overview 2015 URL <http://www8.hp.com/us/en/products/monitors/product-detail.html?oid=7445887&jumpid=reg_r1002_usen_c-001_title_r0001#!tab=features> (2 pages).

"International Preliminary Report on Patentability," for International application No. PCT/US2014/050944 dated Feb. 16, 2016 (12 pages).

"International Search Report and Written Opinion," for International application No. PCT/US2014/050944 dated Feb. 19, 2015 (19 pages).

"Kinect Sensor Allows Surgeons to Manipulate 3D CT Images in Midair," Published Feb. 11, 2011. <https://www.youtube.com/watch?v=id7OZAbFaVI>.

"Stratasys and Vital Images Partner on 3-D Printing," Diagnostic and Interventional Cardiology Dicardiology.com Dec. 14, 2015 URL<http://www.dicardiology.com/product/stratasys-and-vital-images-partner-3-d-printing> (2 pages).

Tilley, Aaron "HP Inc. Is Bringing Its Giant Virtual Reality Display Into Healthcare," Forbes Tech, Dec. 13, 2015 URL <http://www.forbes.com/sites.aarontilley/215/12/03/hp-inc-is-bringing-its-giant-virtual-reality-display-into-the-operating-room/> (2 pages).

"Video: Cardiology Medical Animation—Deployment of Mitral Valve Clip," Published on Jun. 26, 2009, scientificanim777. URL <https://www.youtube.com/watch?v=yET7if-tLtM> (15 pages).

International Search Report and Written Opinion for PCT Application No. PCT/US2017/045925 dated Oct. 13, 2017 (10 pages).

International Search Report and Written Opinion for PCT Application No. PCT/US2017/045931 dated Nov. 2, 2017 (13 pages).

Non Final Office Action for U.S. Appl. No. 15/671,800 dated Oct. 5, 2018 (24 pages).

Final Office Action for U.S. Appl. No. 15/671,800 dated Feb. 6, 2019 (18 pages).

International Preliminary Report on Patentability for PCT Application No. PCT/US2017/045925 dated Feb. 21, 2019 (7 pages).

International Preliminary Report on Patentability for PCT Application No. PCT/US2017/045931 dated Feb. 21, 2019 (10 pages).

Response to Final Rejection dated Feb. 6, 2019, for U.S. Appl. No. 15/671,800, submitted via EFS-Web on Apr. 24, 2019, 9 pages.

Response to Non-Final Rejected dated Oct. 5, 2018, for U.S. Appl. No. 15/671,800, submitted via EFS-Web on Nov. 26, 2018, 9 pages.

Non-Final Office Action for U.S. Appl. No. 15/671,800 dated Jun. 25, 2019 (22 pages).

Response to Non Final Office Action for U.S. Appl. No. 15/671,800, filed Sep. 4, 2019 (11 pages).

* cited by examiner

DISTRIBUTED INTERACTIVE MEDICAL VISUALIZATION SYSTEM WITH USER INTERFACE FEATURES

This application claims the benefit of U.S. Provisional Application No. 62/374,343, filed Aug. 12, 2016, the contents of which are herein incorporated by reference in their entireties.

FIELD

Embodiments herein relate to distributed interactive medical visualization systems with user interface features and related methods.

BACKGROUND

Medical diagnosis and treatment is often aided by, or in some cases based upon, visual observation of one or more portions of a patient's anatomy. Most commonly, this visual observation is performed through direct physical observation of what is visible to the clinician with the unaided eye. In surgical scenarios, this may include visual observation of internal organs.

Various instruments have been configured with optics or electronic imaging cameras to allow visual observation of portions of the patient's anatomy that may otherwise be difficult to see. By way of example, bronchoscopes, endoscopes, and the like have all allowed clinicians to visually observe portions of the anatomy that are otherwise hidden.

Techniques for medical imaging have also greatly extended the ability of clinicians to visually observe portions of a patient's anatomy. Beginning with techniques such as x-ray radiography, and later including techniques such as fluoroscopy, computerized axial tomography (CAT), and magnetic resonance imaging (MRI), the ability to view portions of a patient's anatomy has never been greater. However, in many cases, the images generated by medical imaging systems are two-dimensional and thus require a great degree of skill in order to interpret properly. Some imaging systems provide images that include three-dimensional information, but are rendered on two-dimensional displays causing much of the value of the three-dimensional information to be lost.

SUMMARY

Embodiments herein relate to distributed interactive medical visualization systems, user interface features therefore, and related methods. In a first aspect, a distributed interactive medical visualization system is included having a first video processing circuit, a first central processing circuit in communication with the first video processing circuit, a first communications circuit in communication with the first central processing circuit, and a first user interface generated by the first video processing circuit. The first user interface can include a three-dimensional model of at least a portion of a subject's anatomy from a first perspective, the first perspective configured to be controlled by a first user. The first user interface can further include one or more user representations representing one or more other users, the user representations superimposed within the three-dimensional model, wherein each of the one or more user representations are visually distinct from one another.

In addition to one or more of the preceding or following aspects, or in the alternative to some aspects, in a second aspect, one or more user representations include light pens.

In addition to one or more of the preceding or following aspects, or in the alternative to some aspects, in a third aspect, one or more user representations have different colors from one another.

In addition to one or more of the preceding or following aspects, or in the alternative to some aspects, in a fourth aspect, the three-dimensional model including one or more of patient data gathered in real-time, previously stored patient data, and idealized model data.

In addition to one or more of the preceding or following aspects, or in the alternative to some aspects, in a fifth aspect, information about the first perspective is broadcast across a network.

In addition to one or more of the preceding or following aspects, or in the alternative to some aspects, in a sixth aspect, information about one or more user representations is broadcast across a network.

In addition to one or more of the preceding or following aspects, or in the alternative to some aspects, in a seventh aspect, the first video processing circuit is co-located with a machine displaying the primary user interface.

In addition to one or more of the preceding or following aspects, or in the alternative to some aspects, in an eighth aspect, the first video processing circuit is remotely located from a machine displaying the first user interface.

In addition to one or more of the preceding or following aspects, or in the alternative to some aspects, in a ninth aspect, a distributed interactive medical visualization system is included having a first video processing circuit, a first central processing circuit in communication with the first video processing circuit, a first communications circuit in communication with the first central processing circuit, and a first user interface generated by the first video processing circuit. The first user interface can include a three-dimensional model of at least a portion of a subject's anatomy from a first perspective, the first perspective configured to be controlled by a first user. The first user interface can further include a command interface object, wherein engagement of the command interface object causes the first user interface to display a three-dimensional model of the subject's anatomy from a second perspective.

In addition to one or more of the preceding or following aspects, or in the alternative to some aspects, in a tenth aspect, a distributed interactive medical visualization system is included having a first video processing circuit, a first central processing circuit in communication with the first video processing circuit, a first communications circuit in communication with the first central processing circuit, and a first user interface generated by the first video processing circuit. The first user interface can include a three-dimensional model of at least a portion of a subject's anatomy from a first perspective, the first perspective configured to be controlled by a first user. The first user interface can further include one or more graphical representations of one or more other users who are viewing the same three-dimensional model, wherein each of the one or more graphical representations identify individual users amongst the one or more other users.

In addition to one or more of the preceding or following aspects, or in the alternative to some aspects, in a eleventh aspect, a distributed interactive medical visualization system is included having a first video processing circuit, a first central processing circuit in communication with the first video processing circuit, a first communications circuit in communication with the first central processing circuit, and a first user interface generated by the first video processing circuit. The first user interface can include a three-dimensional model of at least a portion of a subject's anatomy from a first perspective, the first perspective configured to be controlled by a first user. The first user interface can further include a command interface object, wherein engagement of the command interface object causes one or more other user interfaces controlled by one or more other users to switch from being directed by individual other user to being directed by the first user.

In addition to one or more of the preceding or following aspects, or in the alternative to some aspects, in a twelfth aspect, a distributed interactive medical visualization system is included having a first video processing circuit, a first central processing circuit in communication with the first video processing circuit, a first communications circuit in communication with the first central processing circuit, and a first user interface generated by the first video processing circuit. The first user interface can include a three-dimensional model of at least a portion of a subject's anatomy from a first perspective, the first perspective configured to be controlled by a first user. The first user interface can further include a virtual representation of one or more annotations, each annotation having a specific location anchor within the three-dimensional model.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

There are many techniques by which visual anatomical data can be gathered. Techniques can include x-ray radiography, fluoroscopy, computerized axial tomography (CAT), magnetic resonance imaging (MRI), and the like. Traditionally, one challenge in using such information has been that images generated are commonly two-dimensional and require a great degree of skill in order to interpret properly. Some imaging systems provide images that include three-dimensional information, but are rendered on two-dimensional displays causing much of the value of the three-dimensional information to be lost.

Various newer techniques allow for three-dimensional image data to be displayed in a way that appears to the user to reflect three-dimensions. While the techniques vary, they are typically based on the fundamental principle of displaying slightly different images to each eye of the user, allowing the sensation of a three-dimensional image to be experienced by the system user. Display of visual information in three dimensions is a great step forward in allowing users to rapidly learn based on what they are seeing.

Systems and methods for allowing multiple individuals to interact with the same three-dimensional image model at the same time are provided herein. In specific, user interface features are provided herein that can facilitate multiple users viewing the same three-dimensional anatomical model.

Figure 1:
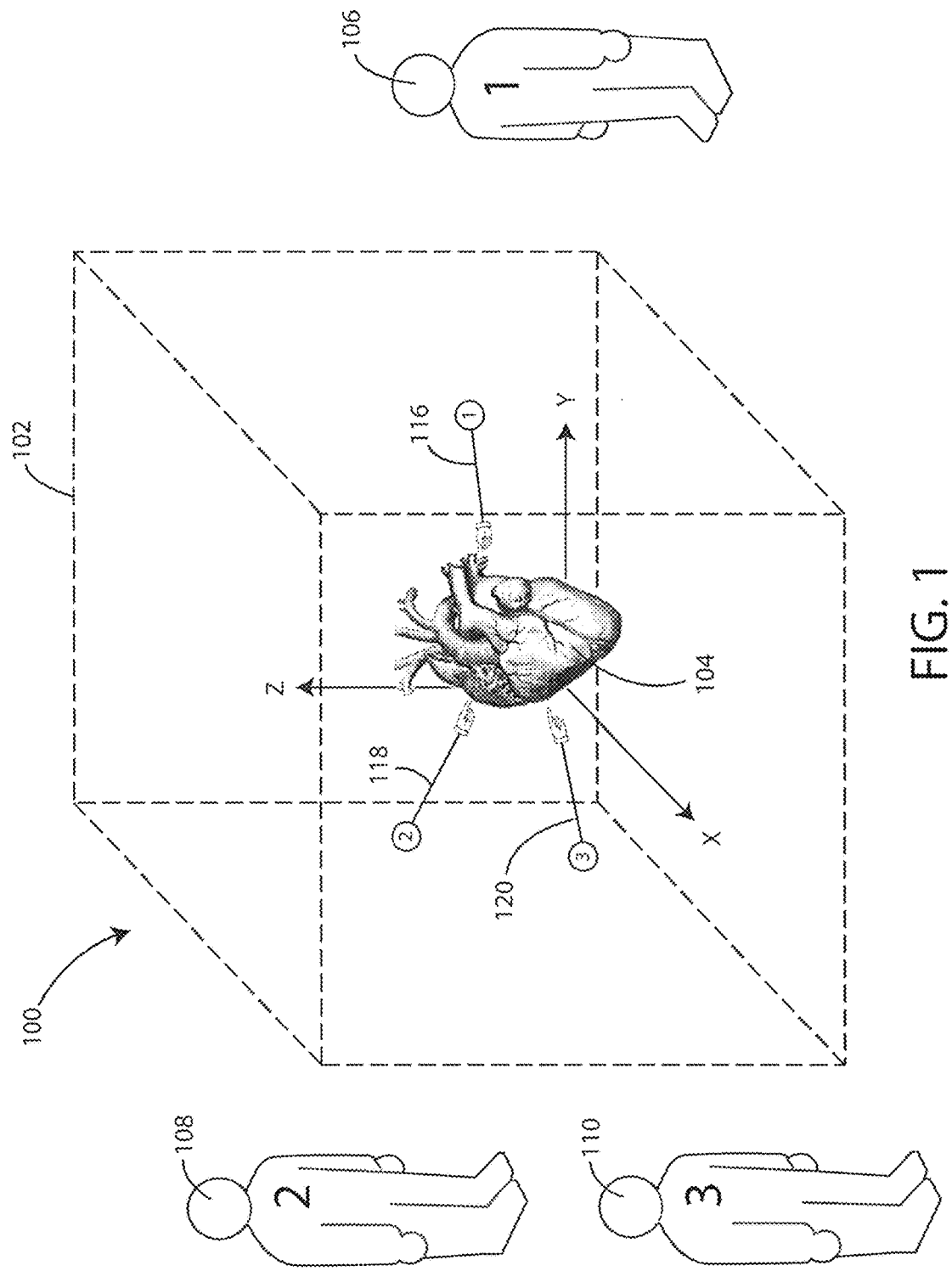
FIG. 1 is a schematic view of aspects of a distributed interactive medical visualization system in accordance with various embodiments herein.

Referring now to FIG. 1, a schematic view is shown of aspects of a distributed interactive medical visualization system 100 in accordance with various embodiments herein. The distributed interactive medical visualization system 100 can include a three-dimensional model 102 of at least a portion of a subject's anatomy 104. The three-dimensional model 102 can extend in the X, Y and Z dimensions. Multiple individuals can interface with the three-dimensional model 102 simultaneously. For example, a first user 106 can be viewing and interacting with the three-dimensional model 102 at the same time as one or more second users 108, 110. In some embodiments, each user can be viewing the model 102 from their own perspective. By way of example, the first user 106 can be viewing the model 102 from a first perspective 116, while a second user 108 can be viewing the model 102 from a second perspective 118 and a third user 110 can be viewing the model 102 from a third perspective 120.

The perspective of each individual user interacting with the model 102 can be defined in various ways. In some embodiments, an individual perspective can include coordinates indicating the point of origin for the individual user's view or vision. This allows the user to "move" through the model as their point of origin changes. In some embodiments, an individual perspective can also include angles indicating the direction that the user is currently looking from their point of origin.

Figure 2:
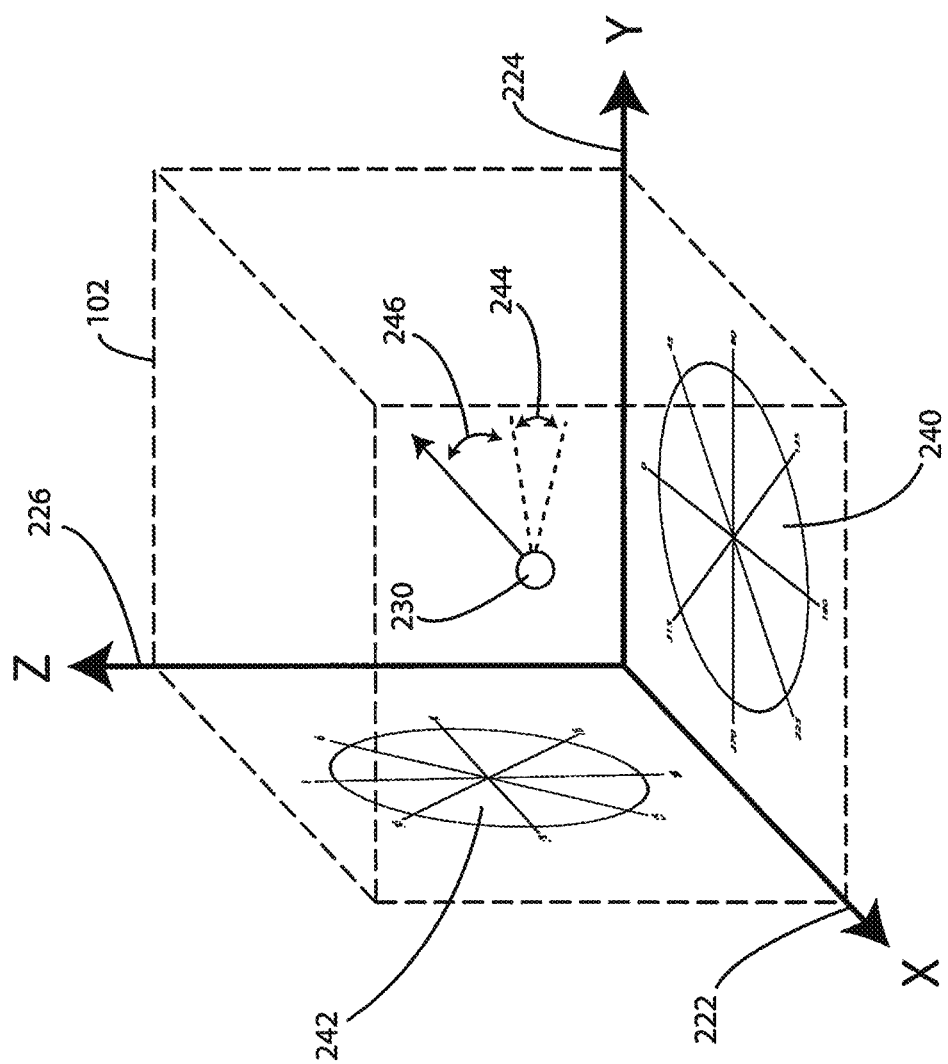
FIG. 2 is a schematic view of a three-dimensional model illustrating an embodiment of a particular user's perspective in accordance with various embodiments herein.

Referring now to FIG. 2, a schematic view is shown of a three-dimensional model 102 illustrating an embodiment of a particular user's perspective. In some embodiments, the particular user's perspective can include a location and a viewing angle. For example, the model can include X (222), Y (224), and Z (226) dimensions. The total volume of the model can be a matter of the product of the maximum magnitude of each of the X, Y and Z dimensions. An individual's perspective can include a location (or point of origin) within the maximum X, Y and Z bounds. For example, point of origin 230 can represent a particular individual's current position within the three-dimensional model. In order to represent a particular user's perspective, the model can also take into account viewing angles. For example, by using a first angle 240 reflective of rotation within the XY plane and a second angle 242 reflective of rotation within the Z plane it is possible to specify any possible directional view within the model 102. As such, a user's perspective can be defined by the point of origin 230, in combination with the XY angle 244 and the Z axis angle 246. While this provides one example of how a user's perspective within a three-dimensional model can be defined, it will be appreciated that there are many other possible ways to precisely describe the user's perspective.

Figure 3:
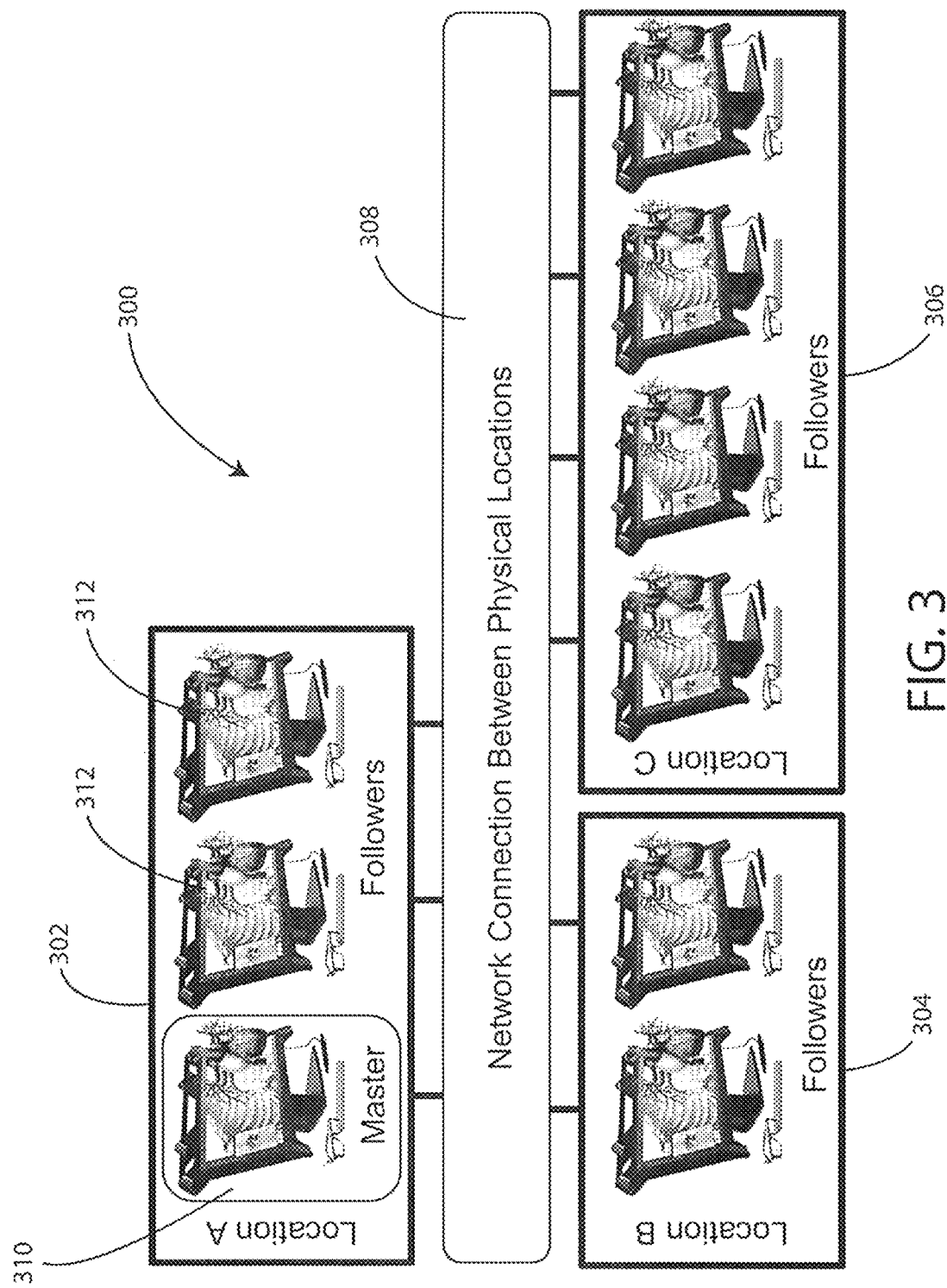
FIG. 3 is a schematic diagram of a distributed interactive medical visualization system in accordance with various embodiments herein.

Interactive medical visualization systems can be "distributed" in that they can be physically distributed across multiple individual machines or workstations. The individual machines or workstations can be in the same physical location or area or they can be in separate physical locations. Referring now to FIG. 3, a schematic diagram is shown of a distributed interactive medical visualization system 300 in accordance with various embodiments herein. In this example, the visualization system 300 includes users in a first location 302 (location A), a second location 304 (location B), and a third location 306 (location C). In some embodiments, the different physical locations may simply be different rooms in the same facility, such as a hospital or a university. In other embodiments, the different physical locations may be miles apart from one another. The locations (302, 304 and 306) can be interconnected via a network connection 308 existing between the disparate physical locations. In this view, the first location 302 includes a master user 310 (or first user, primary user or leader) and two followers 312 (or secondary users). The other locations include only followers. It will be appreciated, however, that in some cases the master user 310 can be in a physical location by themselves. In still other cases, all of the users may be in the same physical location. In some scenarios there may be more than one master user.

The architecture of interactive medical visualization systems herein can vary. In some embodiments, the system can exist in a peer-to-peer type model without a central node or controlling machine. In other embodiments, the system can include a central node, such as an anatomical model server that calculates aspects about the three-dimensional model and various users currently in the model and then sends this information on to individual machines or workstations for rendering. In still other embodiments, video rendering can occur almost entirely on a central node or server (or cluster of servers) and video images can then be pushed to individual workstations which display received video signals (encoded or non-encoded) and which receive and transmit user input.

Figure 4:
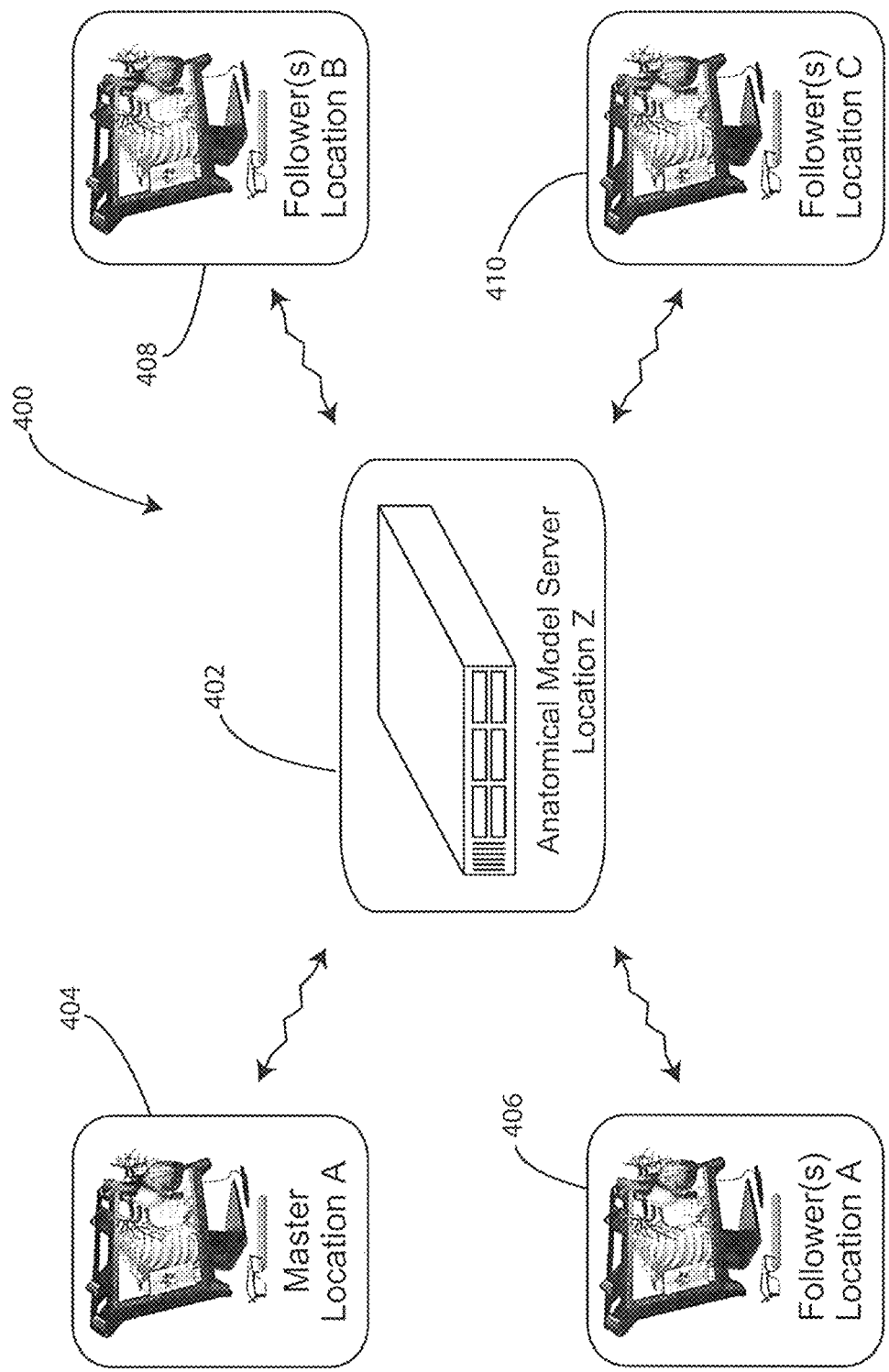
FIG. 4 is a schematic view of a distributed interactive medical visualization system in accordance with various embodiments herein.

Referring now to FIG. 4, a schematic view is shown of a distributed interactive medical visualization system 400 in accordance with various embodiments herein. The system 400 includes a master user 404 (or first user, primary user, or leader) at location A in bidirectional communication with an anatomical model server 402 at location Z. Location Z can be the same or different than location A. The system 400 also includes a follower 406 at location A, a follower 408 at location B, and a follower 410 at location C. In some embodiments, substantial video processing, including but not limited to image or video rendering, occurs on the anatomical model server 402 and video streams are then distributed to individual user nodes. In other embodiments, the anatomical model server 402 serves primarily only to coordinate the interaction between users and the majority of video processing occurs at the level of individual nodes (machines operated by individual users) of the system.

Each individual machine or system can provide or display a user interface for individuals to interface with. The user interface can be generated by a video processing circuit (discussed in greater detail below). The video processing circuit can be local to the user's machine or can be located at a central node or server. The user interface can include various features. By way of example, the user interface can include a representation of the three-dimensional model of at least a portion of a subject's anatomy from a certain perspective. In some cases, the perspective can be configured to be controlled by the system user (first or second, primary or secondary, etc.) through the user interface.

The user interface can include various command interface objects. Command interface objects can include various elements that a user can interact with either directly (such as with a touch screen) or indirectly (such as with a keyboard, a mouse, a pen, or the like either real or virtual). Command interface objects can include, but are not limited to, a button, a menu tree, a slider bar, a dial, or the like. Engagement or actuation of the command interface object by the user can cause various actions or functions to be executed as described in greater detail below.

Figure 5:
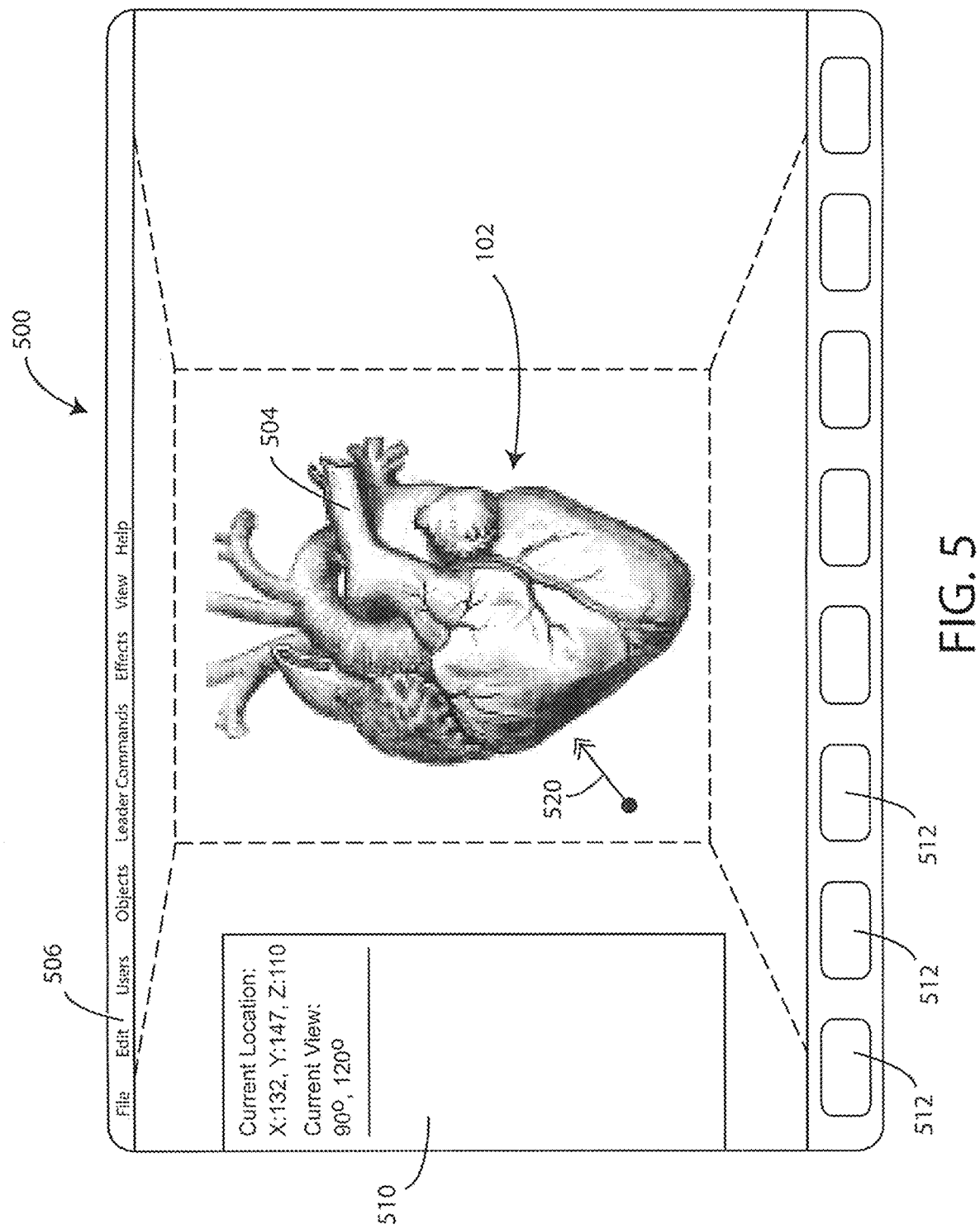
FIG. 5 is a schematic view of an exemplary user interface shown in accordance with various embodiments herein.

Referring now to FIG. 5, a schematic view of an exemplary user interface 500 is shown in accordance with an embodiment herein. The user interface 500 includes a three-dimensional anatomical model 102. The anatomical model 102 includes a three-dimensional image 504 of at least a portion of a patient's anatomy. The user interface can show an icon or other graphical object 520 indicating the position and/or view of another user interacting with the same three-dimensional anatomical model 102.

The user interface 500 can also include a menu bar 506 that can include command interface objects such as menu trees. The user interface 500 can also include one or more command interface objects such as buttons 512. In some embodiments, the user interface 500 can also include an information side bar 510. The information side bar 510 can be selectively shown or hidden and can display information such as the current location and current view of the user interacting with the user interface or information for another selected user. For example, if the user of the system displaying the user interface 500 clicks on the graphical object 520 indicating another user, then that user's information can be displayed in the side bar 510. In some embodiments, instead of a side bar, the same types of information can be displayed on a bar attached to the bottom or top of the screen. In still other embodiments, the same types of information can be rendered within the three-dimensional model itself.

The three-dimensional anatomical model can include various other types of graphical elements rendered to be within the model or portion of the user interface. By way of example, the three-dimensional model can include graphical representations of one or more other users and their respective positions and current views. In addition, objects such as medical devices can be superimposed and/or rendered in the three-dimensional model.

Figure 6:
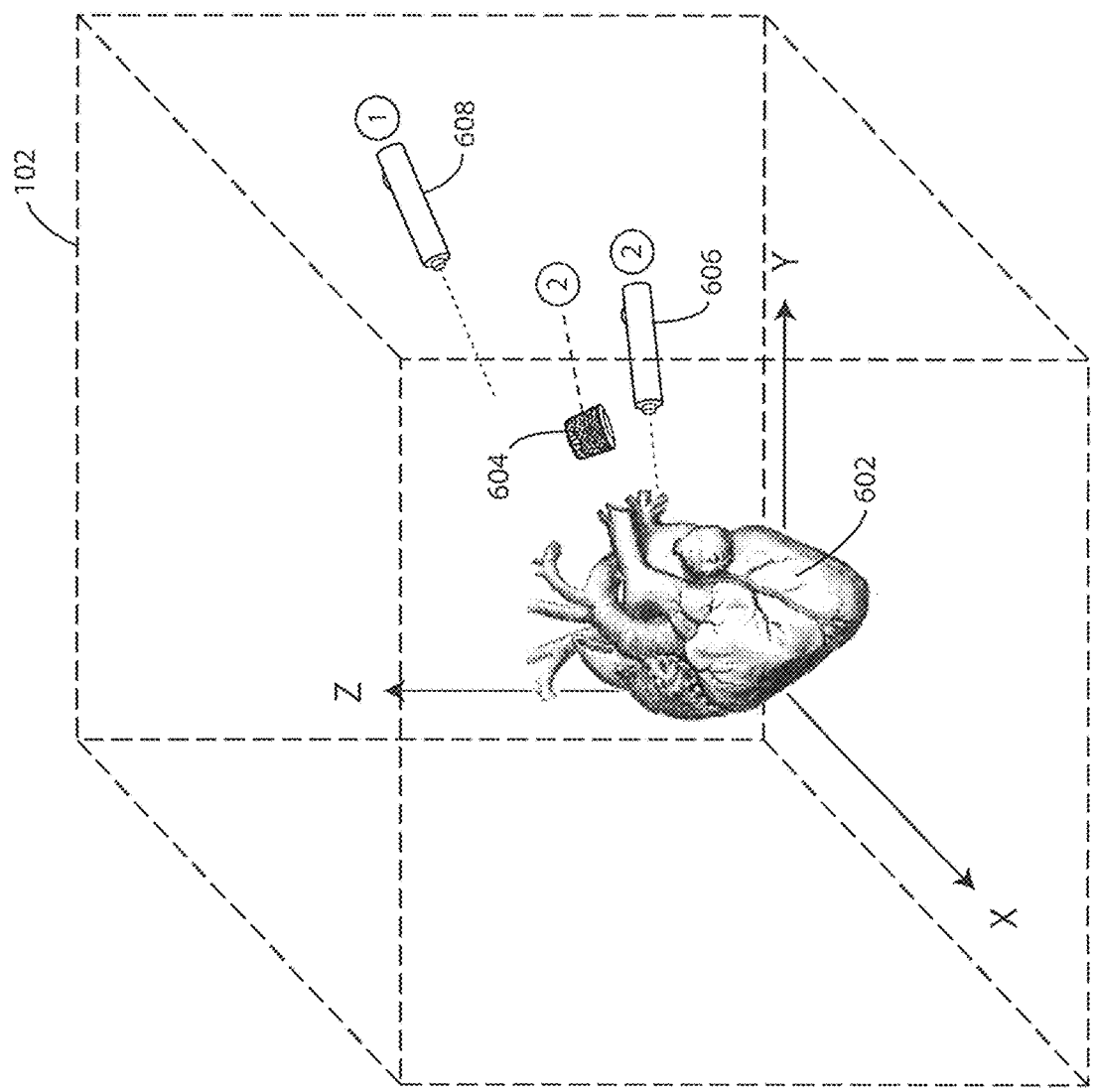
FIG. 6 is a schematic view of a three-dimensional anatomical model in accordance with various embodiments herein.

Referring now to FIG. 6, a schematic view is shown of a three-dimensional anatomical model in accordance with various embodiments herein. The three-dimensional anatomical model can include a visual representation of at least a portion of a patient's anatomy 602. The three-dimensional anatomical model can include a visual representation of a medical device 604. In this case, the medical device 604 is a heart valve. However, it will be appreciated that the medical device can be any sort of medical device including, but not limited to, a stent, an implantable cardiac rhythm management device, a catheter, an embolic protection device, and the like. The user can manipulate the medical device including moving, spinning, and/or deploying the medical device. In this view, the perspective of a first user 608, as represented with a first light pen, is shown along with the perspective of a second user 606, as represented with a second light pen.

As described above, the three-dimensional model can include a view of at least a portion of a patient's anatomy. In addition, the three-dimensional model can include other aspects including representations of medical devices, indications of other users, and general information superimposed into the model. The anatomical visualization can include portions of data from various sources. By way of example, the anatomical visualization can include live visualization data taken from a patient in real-time, visualization data previously recorded from a patient and stored, as well as idealized anatomical model data drawn from general medical knowledge and/or from a population of patients. In some cases, the system can blend portions of data from one or more of these sources in order to create the three-dimensional anatomical model used in various embodiments herein.

Figure 7:
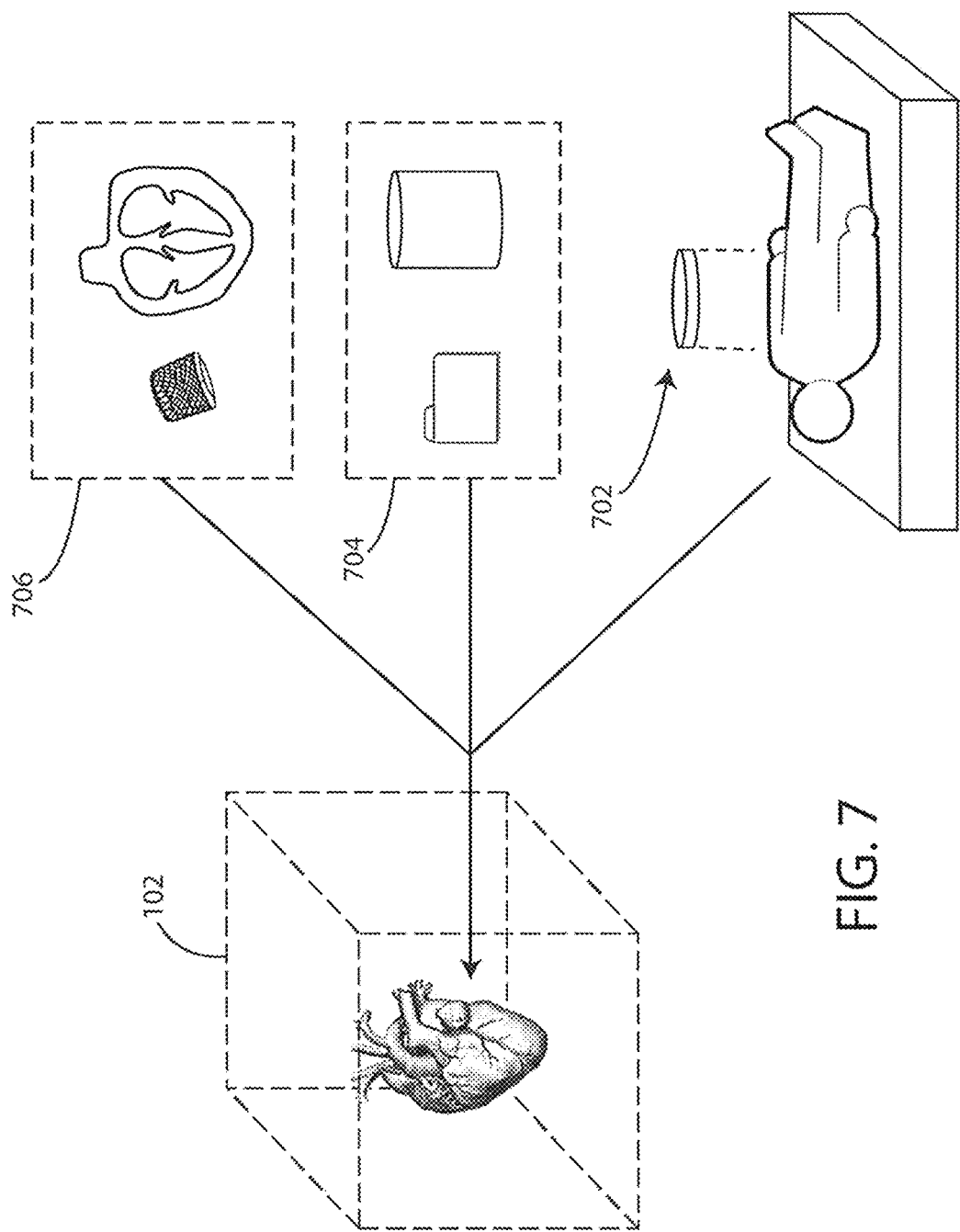
FIG. 7 is a schematic view showing sources of data for use in generating a three-dimensional anatomical model.

Referring now to FIG. 7, a schematic view is shown indicating sources of data for use in generating a three-dimensional anatomical model 102. The sources of data can include patient data gathered in real-time 702, previously stored patient data 704 (such as data stored in files, folders, and/or databases), and idealized model data 706. Patient data gathered in real-time can include data such as medical imaging data including, but not limited to, x-ray radiography data, fluoroscopy data, computerized axial tomography (CAT) data, magnetic resonance imaging (MRI) data, camera data, and the like. Previously stored patient data can include data such as medical imaging data including, but not limited to, x-ray radiography data, fluoroscopy data, computerized axial tomography (CAT) data, magnetic resonance imaging (MRI) data, camera data, and the like. Idealized model data can include idealized models of anatomical structure, including, but not limited to, major organs (heart, lungs, liver, kidneys, brain, etc.), joints, bone structure, musculature, chest cavity, the vascular system, central and peripheral venous systems, the cardiopulmonary system, the lymphatic system, the hepatic system, the renal system, the head and specifically the brain, sinuses, etc. and/or medical devices used in medical procedures including, but not limited to, implants, heart valves, embolic protection devices, stents, grafts, medical instruments, cardiac rhythm management devices, pacemakers, implantable cardioverter defibrillators, cardiac resynchronization therapy devices, ventricular assist devices, and the like. Idealized model data can be stored in CAD file formats including information regarding geometry (wireframe, surface, solid, etc.) or can be stored in other file formats including similar information about the idealized models.

As described above, systems for displaying visual information in three dimensions are typically based on mechanism for providing a first image to one eye of a user and a second image, different than the first, to a second eye of the user. In this manner, the image, as perceived by the user can appear to have depth and therefore appear to be in three-dimensional. In some cases, a separate video image can be provided to each eye of a user through separate video screens or separate portions of a single video screen. In other cases, the separate video screens can be disposed within a headset or glasses.

However, in some cases, a single video screen can be used in can h polarized eyewear. In some embodiments, a stereoscopic image including a left image and a right image that is spatially multiplexed within the stereoscopic image can be presented to a left eye and a right eye respectively of the user of a left polarizing filter and a right polarizing filter. An exemplary approach of this type is described in US 2007/0043466, the content of which is herein incorporated by reference.

It will be appreciated that systems herein can have various form factors in order to provide a user interface including a view of a three-dimensional model of a patient's anatomy. By way of example, the system can include a headset with one or more screens to show separate images to the left and right eye, a screen with a multiplexed left and right image and glasses to cause the left eye to see the left image and the right eye to see the right image, or a similar system. In some embodiments the system can include sensors so as to track the position of a user's head. One approach for tracking the position of a user's head is described in US 2013/0128011, the content of which is herein incorporated by reference.

In some embodiments, each user, or aspects about each user, can be represented (user representations) within the three-dimensional model. The user representations can take many different forms. In some cases user representation can reflect a virtual image of a physical object. For example, in some cases the user can have a pen or light pen as a user input device and a virtual image of the pen, and/or a manifestation of the pen such as a light beam extending from the pen, can be superimposed within the three-dimensional model for others to see. In other cases, the user representation can be contrived, such as being a symbol (such as an arrow, line, etc.), a graphical element, an avatar, or the like.

The user representations of different users can be visually distinct from one another. In this manner, information can be provided to system users regarding other users who are viewing the same three-dimensional model, but from other perspectives. The user representations can be made to be visually distinct from one another in many different ways. For example, a different color can be used to represent each different user. In some cases, a different color can be used to represent each different group of users.

In some cases the use of different colors can be consistent across different user's views of the three-dimensional model. For example, user "X" can be associated with a particular color (hypothetically green) and their user interface object can consistently be that color regardless of which user is viewing the three-dimensional model through their user interface. In other cases, the use of distinct colors can be relative in the sense that user "X" can appear to have a green user representation and other user representations do not have green, but when viewed from a different user's interface, then user "X" can appear to have a blue user representation and other users do not have a blue user representation.

In an embodiment, a distributed interactive medical visualization system is included, the system having a first video processing circuit, a first central processing circuit in communication with the first video processing circuit, and a first communications circuit in communication with the first central processing circuit. The system can also include a first user interface generated by the first video processing circuit, the first user interface including a three-dimensional model of at least a portion of a subject's anatomy from a first perspective, the first perspective configured to be controlled by a first user. The first user interface can also include one or more user representations representing one or more other users, the user representations superimposed within the three-dimensional model, wherein each of the one or more user representations, or groups of user representations, are visually distinct from one another.

In some embodiments, the user interface includes a command or command interface object that allows a user to snap (or jump) to a display of a different perspective of the same three-dimensional anatomical model. The different perspective can represent a fixed or dynamic perspective, a preset perspective, a perspective representing the current perspective of another user, or the like. In some cases, the user interface can present a list or set of other perspectives to which the perspective on the three-dimensional anatomical model can be set to. Selection of an option from the list or set can cause the current perspective to change to the selected perspective. In some embodiments, waypoints or other markers can be superimposed within the three-dimensional anatomical model itself and selection of those waypoints or other markers can initiate the current perspective changing to the selected perspective. In some cases, the markers can represent specific other users.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a first user. The method can further include displaying one or more one or more command interface object(s) that allows a user to snap (or jump) to a display of a different perspective of the same three-dimensional anatomical model.

In an embodiment, a distributed interactive medical visualization system is included, the system having a first video processing circuit, a first central processing circuit in communication with the first video processing circuit, and a first communications circuit in communication with the first central processing circuit. The system can also include a first user interface generated by the first video processing circuit, the first user interface including a three-dimensional model of at least a portion of a subject's anatomy from a first perspective, the first perspective configured to be controlled by a first user. The first user interface can also include one or more user representations representing one or more command interface objects, wherein engagement of the command interface object causes the first user interface to display a three-dimensional model of the subject's anatomy from a second perspective.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a first user. The method can further include displaying one or more user representations including one or more command interface objects, wherein engagement of the command interface object causes the first user interface to display a three-dimensional model of the subject's anatomy from a second perspective.

In some embodiments, the user interface includes representations or identifiers of other users who are viewing the same subject matter. The user-specific representation or identification can appear on the user interface superimposed in the three-dimensional anatomical model so as to identify particular users. In some cases, the user-specific representation or identification can appear on the user interface, but not superimposed in the three-dimensional anatomical model itself. The user-specific identification can be accompanied by various pieces of information. By way of example, the information can include what anatomical feature the other user is currently looking at, from what angle, etc.

In an embodiment, a distributed interactive medical visualization system is included, the system having a first video processing circuit, a first central processing circuit in communication with the first video processing circuit, and a first communications circuit in communication with the first central processing circuit. The system can also include a first user interface generated by the first video processing circuit, the first user interface including a three-dimensional model of at least a portion of a subject's anatomy from a first perspective, the first perspective configured to be controlled by a first user. The first user interface can also include one or more one or more graphical or textual representations of one or more other users who are viewing the same three-dimensional model, wherein each of the one or more graphical or textual representations identify individual users amongst the one or more other users.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a first user. The method can further include displaying one or more graphical or textual representations of one or more other users who are viewing the same three-dimensional model, wherein each of the one or more graphical or textual representations identify individual users amongst the one or more other users.

In some embodiments, different users viewing the same three-dimensional anatomical model can have different roles to allow for different functionality based on role. Roles can be defined in many different ways, but by way of example roles can include those with more functionality (such as a facilitator or leader) and those with less functionality (such as a participant or follower). The functionality can be manifested in many different ways. One example includes an ability to shift between a presentation mode wherein the other system users cannot direct their own views of the three-dimensional anatomical model, but are obligate "followers", and an exploration mode where the other system user can direct their own views of the three-dimensional anatomical model. Other aspects of functionality that can be exclusive to a facilitator or leader can include control over what aspects of a three-dimensional model should be displayed and to whom.

In an embodiment, a distributed interactive medical visualization system is included, the system having a first video processing circuit, a first central processing circuit in communication with the first video processing circuit, and a first communications circuit in communication with the first central processing circuit. The system can also include a first user interface generated by the first video processing circuit, the first user interface including a three-dimensional model of at least a portion of a subject's anatomy from a first perspective, the first perspective configured to be controlled by a first user. The first user interface can also include a command interface object, wherein engagement of the command interface object causes one or more other user interfaces controlled by one or more other users to switch from being directed by individual other user to being directed by the first user.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a first user. The method can further include displaying one or more command interface objects, wherein engagement of the command interface object(s) causes one or more other user interfaces controlled by one or more other users to switch from being directed by an individual other user to being directed by the first user.

In some embodiments, the system can be configured to allow individual users to annotate specific aspects of the three-dimensional anatomical model they are viewing or have viewed. Such annotations can be done so that the annotation is private (annotations only visible to the creator), semi-public (at least portions of the annotations are visible to others or to specific groups of others), or fully public (all content visible to all). The annotations can include audio, graphical (including pictures, video and other graphical objects) and/or textual information. The annotations can have a location anchor such as a particular point within the three-dimensional model (which can have X, Y, and Z specificity), a particular region, a particular anatomical feature, or the like. In some cases, however, the annotations are not anchored to any particular thing. In some cases, the annotations include information that is visible whether other users select the annotations or not. In other cases, the annotations include information that only becomes visible if other users actually select the annotations.

In an embodiment, a distributed interactive medical visualization system is included, the system having a first video processing circuit, a first central processing circuit in communication with the first video processing circuit, and a first communications circuit in communication with the first central processing circuit. The system can also include a first user interface generated by the first video processing circuit, the first user interface including a three-dimensional model of at least a portion of a subject's anatomy from a first perspective, the first perspective configured to be controlled by a first user. The first user interface can also include a virtual representation of one or more annotations, each annotation having a specific location anchor within the three-dimensional model.

In an embodiment, a method for displaying a three-dimensional model for multiple users is included. The method can include generating a first user interface with a first video processing circuit, the first user interface including a three-dimensional model of at least a portion of a subject's anatomy from a first perspective, the first perspective configured to be controlled by a first user. The method can further include displaying one or more one or more annotations, each annotation having a specific location anchor within the three-dimensional model.

In some embodiments, the system can include a user interface displaying a visual depiction of an actual physical space (such as an operating room) along with information superimposed thereon such as various elements described elsewhere herein. As such, a physical room and/or a real image of a patient can be viewed along with various graphical enhancements superimposed on the image thereof to enable various pieces of functionality, including for example some of the aspects discussed above. By way of example, the user interface of a particular user can include an image of an actual patient in an operating room along with a user representation of another user viewing the same real image indicating from where and from what perspective they are viewing the same real image. As another example, a first user can create annotations that can be virtually superimposed within the three-dimensional model that can be visible to other users viewing the same real image.

It will be appreciated that the operations included in methods herein are not limited to a particular progression of events unless otherwise noted. Any progression is appropriate that allows the technology discussed herein to be realized.

In some embodiments, the invention includes a device including a graphical display and a machine-readable medium comprising instructions. The instructions can perform various operations when implemented by one or more processors. By way of example, the operations can include those in accordance with methods as described herein. The machine-readable medium can include random access memory (RAM), read-only memory (ROM), magnetic data storage media, optical data storage media, flash memory and the like.

Figure 8:
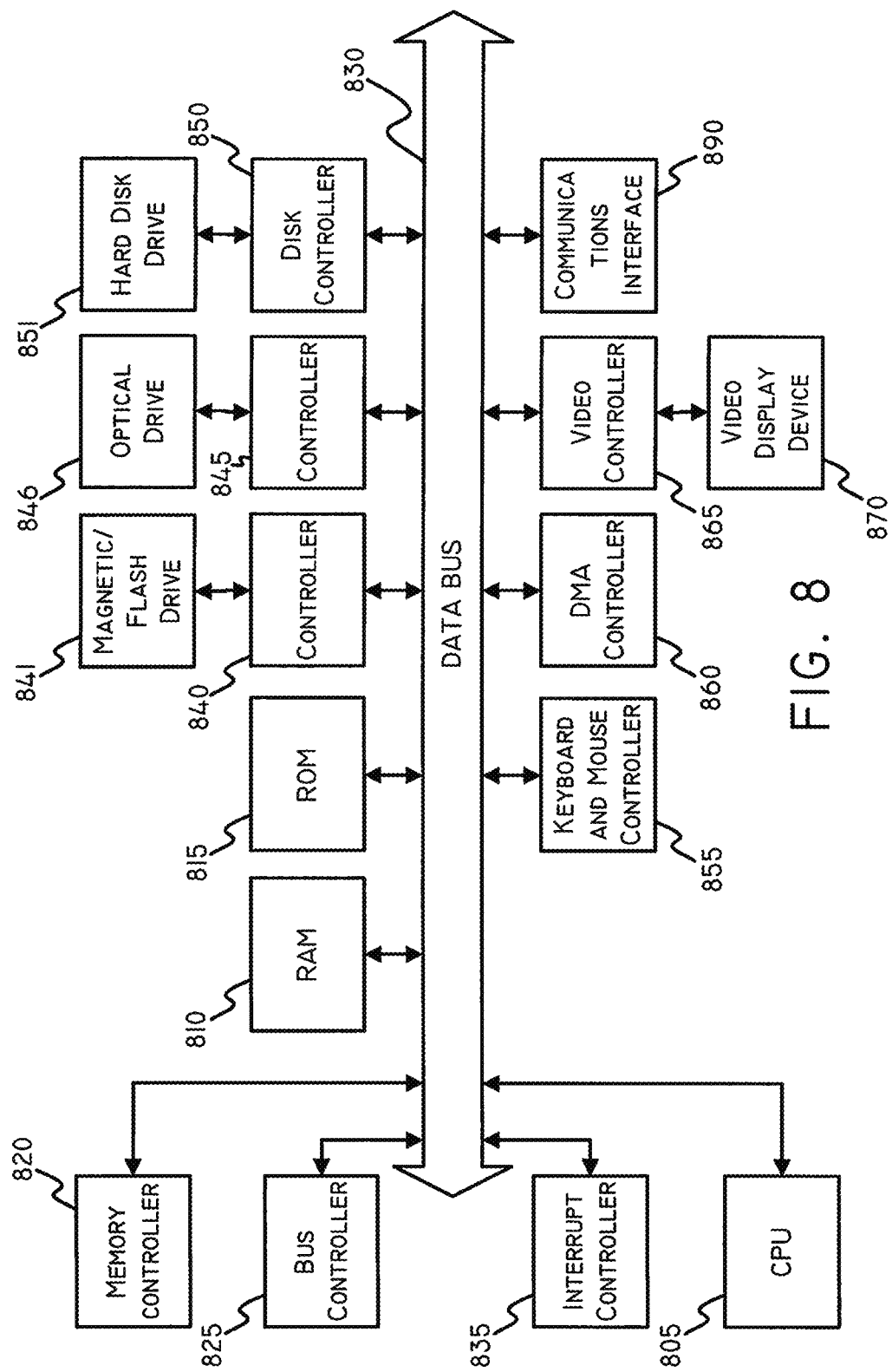
FIG. 8 is a diagram of various components in accordance with some embodiments herein.

Devices to display three-dimensional models of at least a portion of a subject's anatomy and/or user interfaces for the same can include components common to many computing devices. Referring now to FIG. 8, a diagram of various components is shown in accordance with some embodiments. The system can include a central processing circuit that can include various components such as a central processing unit. By way of example, the system can include a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by a magnetic or flash memory drive 841 including removable or non-removable media, which is connected to bus 830 by controller 840, an optical drive such as CD-ROM or DVD drive 846, which is connected to bus 830 by controller 845, and/or hard disk drive 851 (magnetic or solid state), which is connected to bus 830 by controller 850. In some embodiments, mass storage can be provided by a device connected through a universal serial bus (USB), eSATA, FireWire, or Thunderbolt interface or other type of connection. User input to the programmer system may be provided by a number of devices. For example, a keyboard and mouse can be 910 connected to bus 830 by keyboard and mouse controller 855. DMA controller 860 is provided for performing direct memory access to system RAM 810. In some embodiments user input can be provided by a pen, light pen, glove, wearable object, gesture control interface, or the like.

A video processing circuit can be included and can generate a user interface. The video processing circuit can include a video controller 865 or video output, which controls video display 870. In some embodiments, the video controller 865 can also include one or more graphical processing units (GPUs). The video processing circuit can be in communication with the central processing circuit.

The system can also include a communications interface 890 or communications circuit which allows the system to interface and exchange data with other systems and/or servers. The communications circuit can be in communication with the central processing circuit. In some embodiments, the communications interface 890 can include a network interface card or circuit to facilitate communication with a packet switched (such as IP) or other type of data network.

It will be appreciated that some embodiments may lack various elements illustrated in FIG. 8. In addition, the architecture shown in FIG. 8 is merely one example of how discrete components can be arranged and other architectures are explicitly contemplated herein.

In addition to, or instead of, the components described with respect to FIG. 8, it will be appreciated that the system can also include a microcontroller, a programmable logic controller (PLC), an ASIC, an FPGA, a microprocessor, or other suitable technology.

The video processing circuit (either locally or on a remote node) can generate a 3D (or fewer or more dimensions) image based on information including one or more of geometry, viewpoint, texture, lighting and shading information, and other information described above. In some embodiments, information for rendering an image is combined within a scene file. The term "graphics pipeline" can be used to refer to the sequence of steps used to create a 2D raster representation of a 3D scene. The video processing circuit can execute one or more steps of the graphics pipeline. The video processing circuit can also include one or more physical components used in the graphics pipeline. Using the information described above, the graphics pipeline can include one or more stages of creating a scene out of geometric primitives, modelling and transformation, camera transformation, lighting, projection transformation, clipping, scan conversion or rasterization, and texturing and fragment shading. In various embodiments, other operations can also be performed. In various embodiments, the graphics pipeline can use OpenGL, DirectX, or other protocols.

Figure 9:
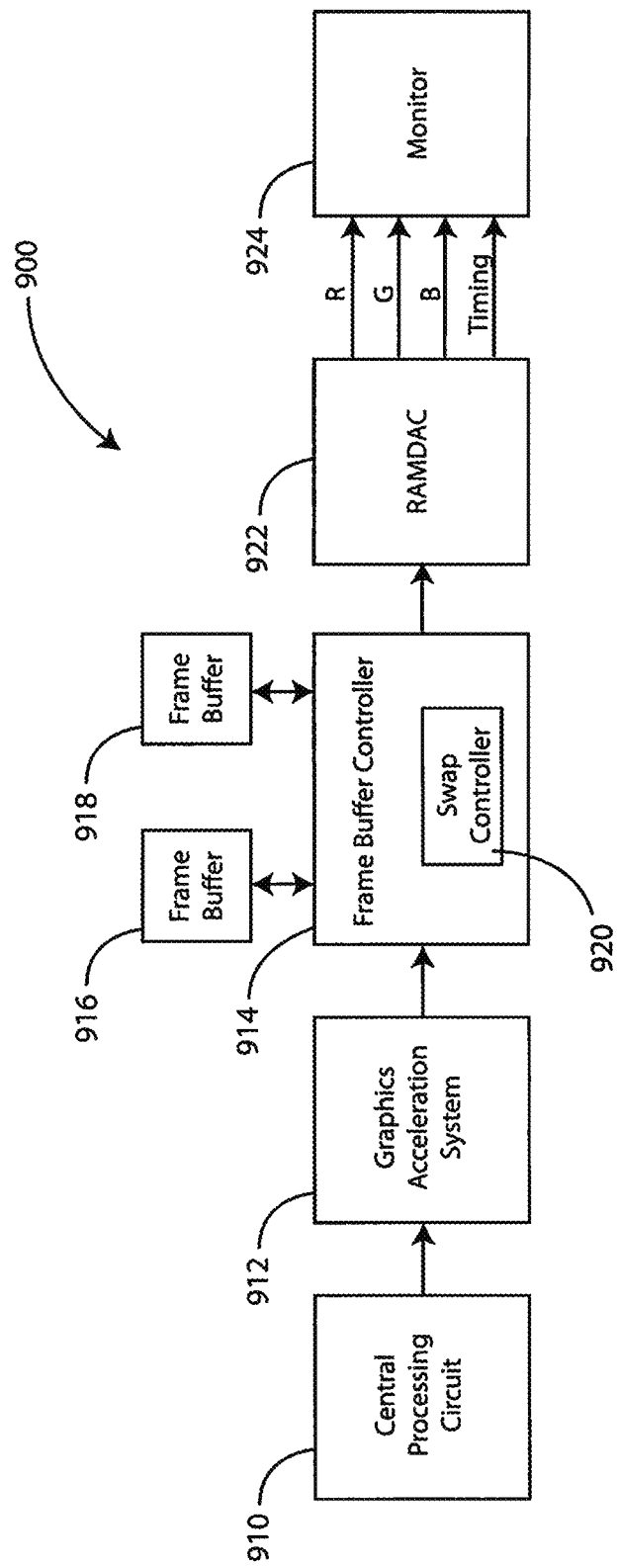
FIG. 9 is a diagram of various components of an exemplary graphics pipeline in accordance with various embodiments herein.

It will be appreciated that various forms of graphics pipelines can be used. As just one example, an exemplary computer graphics pipeline 900 is shown in FIG. 9. In this example, a host computing system or central processing circuit 910 (which can be local or on a remote node) runs system and application software that is capable of modeling a scene in terms of polygon vertices, color, lighting, textures and so on. Central processing circuit 910 sends this information to graphics acceleration system 912 (which can be local or on a remote node). Graphics acceleration system 912 can render the modeled scene by generating pixel data for storage in a frame buffer memory. The contents of the frame buffer memory can be continually read by a random access memory/digital-to-analog converter ("RAMDAC") module 922 which typically contains color or gamma correction lookup tables and drives a display monitor 924. Alternatively, central processing circuit 910 may generate the pixel data without a graphics acceleration system and write the pixel data into the frame buffer directly.

In some cases, a technique known as double buffering can be used. In double buffering, two frame buffers 916 and 918 are provided instead of a single frame buffer. In this manner, the central processing circuit 910 or graphics acceleration system 912 can write pixel data into one frame buffer (the "non-viewable" or "back" buffer) while RAMDAC module 922 and monitor 924 display pixel data previously written into the other frame buffer (the "viewable" or "front" buffer). The effect of this technique is to reduce tearing and other unwanted visual artifacts that are introduced into an image when the contents of a frame buffer are changed while the contents of the same frame buffer are being displayed. In systems that use two buffers, a frame buffer controller 914 can be used to coordinate which buffer will be viewable and which will be non-viewable at any given moment. Specifically, a swap controller 920 within frame buffer controller 914 can indicate when it is safe to stop displaying the contents of one frame buffer and to start displaying the contents of the other frame buffer. Typically, swap controller 920 will indicate that it is safe to swap frame buffers at the moment when (1) the graphics pipeline has finished rendering pixel data into the non-viewable buffer, and (2) the current raster position of the display is not within the window of interest. In full-screen graphics, buffer swapping normally occurs only during a vertical retrace, however it can be performed at various times. In windowed graphics, buffer swapping might occur at any time when the raster is not within the window of interest.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A distributed interactive medical visualization system comprising:
 a first video processing circuit; a first central processing circuit in communication with the first video processing circuit;

a first communications circuit in communication with the first central processing circuit;

a first user interface generated by the first video processing circuit, the first user interface including a three-dimensional model of at least a portion of a subject's anatomy from a first perspective, the first perspective configured to be controlled by a first user; and one or more user perspective representations comprise a point of origin for a user and an angle indicating a direction that the user is currently viewing the three-dimensional model from their point of origin.

2. The distributed interactive medical visualization system of claim 1, the one or more user perspective representations comprising light pens.

3. The distributed interactive medical visualization system of claim 1, the one or more user perspective representations having different colors from one another.

4. The distributed interactive medical visualization system of claim 1, the three-dimensional model including one or more of patient data gathered in real-time, previously stored patient data, and idealized model data.

5. The distributed interactive medical visualization system of claim 1, wherein information about the first perspective is broadcast across a network.

6. The distributed interactive medical visualization system of claim 1, wherein information about the one or more user representations is broadcast across a network.

7. The distributed interactive medical visualization system of claim 1, wherein the first video processing circuit is co-located with a machine displaying the first user interface.

8. The distributed interactive medical visualization system of claim 1, wherein the first video processing circuit is remotely located from a machine displaying the first user interface.

9. A distributed interactive medical visualization system comprising:
   a first video processing circuit;
   a first central processing circuit in communication with the first video processing circuit;
   a first communications circuit in communication with the first central processing circuit;
   a first user interface generated by the first video processing circuit, the first user interface configured to be directed by a first user and including
   a three-dimensional model of at least a portion of a subject's anatomy from a first perspective;
   a second user interface configured to be controlled by a second user, the second user interface displaying the three-dimensional model from a second perspective;
   a user perspective representation of the second user displayed on the first user interface, wherein the user perspective representation comprises a point of origin for the second user and an angle indicating a direction that the second user is currently viewing the three-dimensional model from their point of origin; and
   a command interface object displayed on the first user interface, wherein engagement of the command interface object causes the first user interface to display the three-dimensional model of the subject's anatomy from the second perspective.

10. The distributed interactive medical visualization system of claim 9, wherein engagement of the command interface object causes the second perspective to switch from being directed by the second user to being directed by the first user.

11. The distributed interactive medical visualization system of claim 9, the three-dimensional model including one or more of patient data gathered in real-time, previously stored patient data, and idealized model data.

* * * * *